United States Patent [19]

Malmgren

[11] Patent Number: 4,620,451

[45] Date of Patent: Nov. 4, 1986

[54] CELLULOSE PULP SAMPLING AND CLEANING DEVICE

[75] Inventor: Kjell A. Malmgren, Husum, Sweden

[73] Assignee: Mo och Domsjo Aktiebolag, Ornskoldsvik, Sweden

[21] Appl. No.: 666,518

[22] Filed: Oct. 30, 1984

[30] Foreign Application Priority Data

Nov. 1, 1983 [SE] Sweden ............................. 8305989

[51] Int. Cl.[4] .............................................. G01N 1/00
[52] U.S. Cl. .................................... 73/863.24; 162/60
[58] Field of Search ........... 73/863.01, 863.21, 863.23, 73/863.24, 863.71, 863.81, 864.81, 864.83; 162/49, 60, 198, 263

[56] References Cited

U.S. PATENT DOCUMENTS

| 1,705,907 | 3/1929 | De Witt | 162/60 |
| 2,746,297 | 5/1956 | Martin | 162/263 |
| 3,595,038 | 7/1971 | Bergholm et al. | 162/60 |
| 3,674,434 | 7/1972 | Pottenges | 162/49 |
| 4,154,644 | 5/1979 | Ericsson | 162/60 |

FOREIGN PATENT DOCUMENTS 948532  6/1974  Canada ................................. 162/49

Primary Examiner—Stewart J. Levy
Assistant Examiner—Robert R. Raevis

[57] ABSTRACT

A cellulose pulp fiber sampling and cleaning device for preparing clean pulp fiber samples for automatic analysis of cellulose pulp fiber properties, comprising a pulp sample receptacle having a housing; an elongated pulp fiber sample chamber therein, with fluid passage openings at each end; liquid-permeable and pulp fiber-impermeable material covering each end opening; ports in the housing communicating with the lowest portion of the chamber intermediate the two ends and with each end of the chamber on the outside of the liquid-permeable pulp fiber-impermeable material; and valves controlling flow through the ports; means for introducing and withdrawing washing liquor through the ports at each end of the chamber; and means for introducing and withdrawing pulp fiber suspension and withdrawing cleaned pulp fibers through the port intermediate the two ends.

6 Claims, 3 Drawing Figures

CELLULOSE PULP SAMPLING AND CLEANING DEVICE

Automated techniques have made it possible to determine, either continuously or intermittently, the different properties of pulp directly in the pulping mill. In order to determine the lignin content of chemical pulp fibers subsequent to a cooking stage, or subsequent to a bleaching stage, it is first necessary to free the pulp fibers from cooking liquor, or bleaching liquor, respectively. Preferably, impurities should be removed from the pulp fibers rapidly and effectivly to obtain a practically pure pulp. Ways of doing this have been proposed.

According to one proposal, pulp containing impurities in the form of waste cooking liquor and undigested material (shives) is fed to a rotating, open-ended frustoconical drum. The drum wall is of wire cloth, and is divided into two halves, one narrower and the other wider. The narrower part of the drum is covered with a wire cloth whose mesh is finer than the mesh of the wire cloth covering the wider part. The pulp is fed through a pipe to the narrower part. Washing liquid is supplied through another pipe, and is sprayed over the pulp on the wire cloth. In this way, the waste cooking liquor is washed from the pulp, and passes through the wire, while the pulp fibers remain in the drum. The contaminated washing liquid is discharged to a waste outlet, via a collecting vessel located beneath the frustoconical part. Because the drum is of conical configuration and is rotated, the pulp fibers are advanced along the drum wall to the wider part of the drum. This part is covered with a wire cloth which permits the pulp fibers to pass therethrough but not the undigested material. Washing liquid is also supplied to this part of the drum, through a perforated pipe, for the purpose of facilitating the separation of the pulp fibers from the undigested material. The undigested material is discharged at the end of the wider part, while the pulp fibers are collected in a vessel located below the drum. The pulp fibers are now ready for analysis, for example, to determine the lignin content of the fibers.

However, this apparatus, in common with other open apparatus into which air can enter freely, is plagued with foaming. Foaming prolongs washing time, and greatly increases the quantity of washing liquid required. Furthermore, when the foam spills over, some of the pulp fibers may be lost with the foam.

In order to determine the various properties of pulp directly in the pulping plant, it is often necessary to remove impurities present in the pulp suspension from the sample, for example, cooking waste liquor and bleaching waste liquor, prior to analysis. As a practical matter, it has been found extremely difficult to design apparatus in which the impurities can be removed rapidly and effectively. Such apparatus nonetheless is a prerequisite for the successful automatic analysis of pulp samples with respect to a number of pulp properties.

In accordance with the present invention, a device is provided for preparing clean pulp fiber samples for automatic analysis of cellulose pulp fiber properties, comprising:

(a) a pulp sample receptacle having
 (i) a housing;
 (ii) an elongated pulp fiber sample chamber therein, open at each end;
 (iii) liquid-permeable and pulp fiber-impermeable material covering each open end;
 (iv) ports in the housing communicating with the chamber intermediate the two ends; and with each end of the chamber on the outside of the liquid-permeable pulp fiber-impermeable material; and
 (v) valves controlling flow through the ports;
(b) means for introducing and withdrawing washing liquor through the ports at each end of the chamber; and
(c) means for introducing and withdrawing pulp fiber suspension and withdrawing cleaned pulp fibers through the ports intermediate the two ends.

In a preferred embodiment, the device comprises a U-shaped tube with the two open ends covered with a liquid-permeable and pulp-impermeable material; to the three ports of which intermediate the two ends are connected three conduits which incorporate valves, one conduit for the introduction of pulp suspension, one conduit for the discharge of surplus pulp suspension, and one conduit for the removal of pulp freed from impurities; while each of the ends are connected to a washing-liquid supply conduit with a valve incorporated therein, and connected to a branch conduit which is provided with a valve and which opens into a waste conduit, which system of conduits, connected alternately to one or the other of said ends, for passage of the washing liquid through the pulp sample, while removing impurities therefrom, and the removal of contaminated washing liquid alternately through one or the other of said ends, and through the waste conduit.

Because of this design, air is unable to enter the device, which means that the quantity of washing liquid required can be kept low, which results in rapid and effective washing of the pulp without appreciable or even any foaming. The supply of washing liquid alternately to one or the other end of the tube enables impurities to be removed effectively. As a result of this alternating supply, the pulp fibers do not tend to pack and form an impermeable plug, and neither are pockets of channels formed, which interfere with penetration of the pulp suspension by washing liquid. Furthermore, the device has no motors or other movable parts, so that it is reliable in operation, and has low maintenance. This latter is of the greatest significance in the analysis of the various pulp properties directly in the pulp manufacturing process, as opposed to laboratory analyses.

Preferred embodiments of the device are shown in FIGS. 1 and 2, in which

Figure 1:
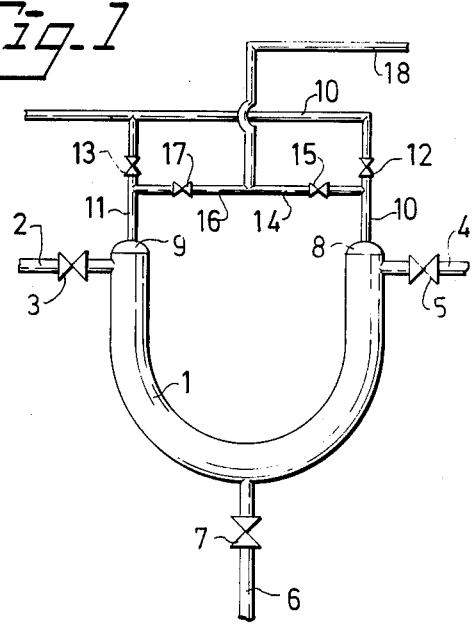
FIG. 1 shows a side view of a U-tube type of device.

While the devices shown in the drawings each have housings and elongated sample chambers in the form of tubes, any type of housing having an elongated sample chamber can be used.

The conduit for supplying the pulp suspension from the pulp supply at a withdrawal or take-out station is preferably connected to the device near one end of the elongated sample chamber, and consequently the conduit for discharging surplus pulp suspension is preferably connected to the device near the outer end of the chamber. The pulp sample is introduced into the chamber by opening a valve in the respective aforementioned conduits, so that the pulp suspension flows through into the chamber. When a given sample quantity of the pulp has been fed into the chamber, determined by the volume of the chamber and the pulp concentration, the valves are closed.

According to one preferred embodiment of the invention, the ends of the chamber are located at a higher level than the remainder of the chamber. According to a particularly preferred embodiment, the tube has a U-shape or V-shape. The conduit for removing the cleaned pulp fiber sample is preferably connected to the tube at its lowermost point, thereby facilitating removal of the cleaned sample. Although the tube and the various conduits may have any suitable cross-sectional shape, they are preferably circular in cross-section.

The liquid-permeable and pulp-impermeable material with which the two open ends of the tube are covered has the form, for example, of wire cloth or gauze made of metal, plastics, glass, or other inert material, or a perforated (slots, holes) plate. It is also possible to use a porous, sintered material. When using wire cloth, it has been found that the mesh openings should be less than 0.4 mm, suitably less than 0.2 mm and preferably less than 0.15 mm.

Connected at each end of the tube outside the permeable mesh is a conduit (which has a valve incorporated therein) for supplying washing liquid, for example pure water or slightly contaminated water, i.e. water having low potassium permanganate consumption. That part of the conduit located between the tube and the valve is also used for carrying away contaminated washing liquid. A branch conduit which incorporates a valve is connected to each of said conduits. These two branch conduits are, in turn, connected to a waste conduit.

When removing the impurities from the pulp sample, for example when washing out waste cooking liquor, the valve on the washing-liquid supply conduit at one end of the tube is opened, while the valve on the other supply conduit is closed. The valve on the branch conduit at one end of the tube is closed, while the valve on the other branch conduit is opened. As a result washing liquid is forced from the first tube-end through the whole of the pulp suspension cylinder, and takes up impurities and carries the impurities to and through the other end of the tube, for transportation to the waste conduit, via the first portion of the corresponding supply conduit with connected branch conduit. This washing continues for a selected time, for example, from 1 to 10 seconds. The flow direction of the washing liquid is then changed by opening the two valves which were previously closed and closing the two valves which were previously opened. In this way, washing liquid is supplied alternately in one and then in the opposite direction, the time taken for each washing stage and the number of directional changes made, i.e. the number of washing stages, depends upon the type of pulp being treated, the type of impurity or impurities present in the pulp, the amount of pulp being treated, and the difficulty in removing the impurity or impurities. The total washing time is normally between 1 and 7 minutes.

Subsequent to cleaning the pulp sample, the valve located in the lower part of the tube is opened, as are also the valves on the two supply conduits, so that the pulp samples can be flushed into a vessel located beneath the device, or conveyed directly to an analysis apparatus through a conduit.

As will be understood, the device according to the invention can be modified within the scope of the concept of the invention. For example, the pulp suspension can be supplied to the tube and removed from the tube through more than one conduit. This also applies to the supply of washing liquid to the tube, and the removal of contaminated washing liquid.

The device is applicable to any cellulose pulp which contains lignin. Examples of lignin-containing pulps include chemical pulp, semichemical pulp, thermomechanical pulp and mechanical pulp.

The device according to the invention can be used in any stage of the pulping process. It is desirable to be able to determine the lignin content of the pulp in different process stages, so that the various stages of manufacturing cellulose pulp can be well controlled. The device according to the invention can be used for all such analyses. For example, the device can be coupled to a sampling conduit located after the digester and downstream of the screening stage, also downstream of the alkali extraction stage and bleaching stage. If the device is to be coupled directly downstream of the digester, the flow of pulp suspension must first be passed through a coarse screen, for removal of undigested material. In these cases, the impurity comprises cooking waste liquor or bleaching waste liquor. It is also necessary to remove these impurities in the case of other analyses, for example, analysis for directly evaluating the brightness of the pulp. In other instances, it may be of interest to remove, for example, fines (short fiber fraction, which are caused to pass through the wire cloths) prior to making the analysis.

FIG. 1 illustrates a U-tube device according to the invention:

Connected to one end of the U-tube 1 is a conduit 2. The tube and the conduit (including all other conduits) can be made of any liquid-impermeable material whatsoever, such as metal, glass, and plastic. The conduit 2 has a valve 3 near the end 1a of the tube 1. Connected to the opposite end 1b of the tube 1 is a conduit 4 with valve 5 near the end 1b. A conduit 6 having a valve 7 is connected to the bottom 1c of the tube 1. Each of the ends 1a, 1b of the tube 1 is covered with a respective wire cloth or gauze 8 and 9, attached directly to the tube. In order to make these end coverings sufficiently stable, it has been found advantageous to form them from an inner, denser wire cloth (mesh size 0.149 mm) and an outer, coarser wire cloth, used in a supporting capacity.

Conduits 10 and 11, having incorporated therein valves 12 and 13, are connected respectively to end coverings 8 and 9. The conduit 10 has connected thereto a branch conduit 14 incorporating a valve 15, while a branch conduit 16 incorporating a valve 17 is connected to the conduit 11. The branch conduits 14 and 16 open into a waste conduit 18.

In use, the valve 3 is opened, so as to permit pulp suspension to flow through the conduit 2 into the tube 1. At the same time, the valve 5 in the conduit 4 is opened. During this stage, the valve 7 in the conduit 6 is closed, and remains closed during the whole of the subsequent washing stage. This means that the pulp suspension flows through and fills the tube 1. The valves 3 and 5 are then closed.

The next stage involves the supply of washing liquid to the tube, this supply being initially effected through the end covering 8, for example. During this stage, the valve 12 is open, while the valve 13 is closed. The valve 15 is also closed, while the valve 17 is opened. During a time period of some seconds, washing liquid is permitted to pass through the pulp suspension in the tube. In this way, impure suspension liquor is exchanged for washing liquid, and the impure liquor is forced through the wire-cloth end covering 9, and through the lower part of the conduit 11, up through the open valve 17 in conduit 16, to the waste conduit 18. After several seconds of washing, the valves 13 and 15 are opened, while the valves 12 and 17 are closed. As a result the washing liquid is passed through the end covering 9 and contaminated washing liquid is taken out through the waste conduit 18, via the end covering 8, the conduit 10 and the conduit 14.

It has been found that rapid changes in the direction in which washing liquid is supplied results in a rapid and effective cleaning of impurities from the pulp. One contributory cause to the good result obtained is thought to be that the rapid changes in the flow direction of the suspension liquid prevent the pulp fibers from agglomerating and forming a difficult-to-penetrate plug. When it is known, as a result of experience, that the pulp is sufficiently clean, i.e. after a given period of time has lapsed, the valves 15 and 17 are closed, and the valves 7, 12 and 13 opened. This causes the pulp sample to be flushed from the tube, at the bottom 1c, via the conduit 6, to an apparatus for automatically determining the lignin content of the sample, for example.

Although the various valves can be opened and closed manually, these opening and closing functions are preferably automated electronically, for example with the aid of a microprocessor arranged to transmit signals to pneumatically controlled valves. The conduit 2 may be advantageously connected directly to a sample removing device, which in turn is connected to a pulp-conveying line in the plant.

Figure 2:
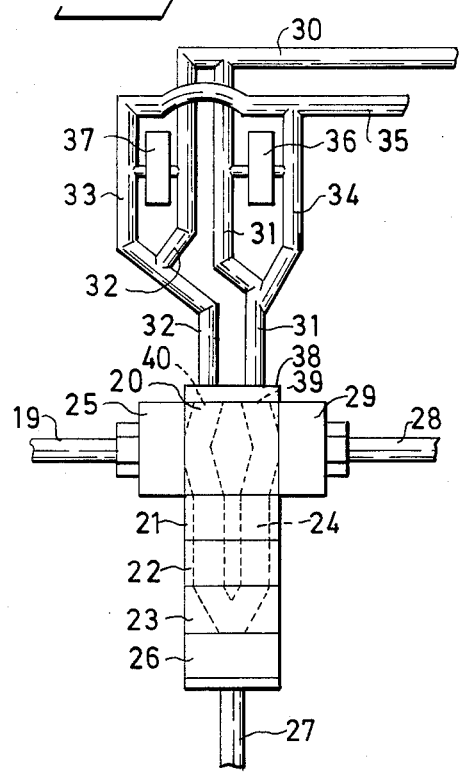
FIG. 2 shows a modular V-type of device.

FIG. 2 illustrates a modular V-type device according to the invention.

In this embodiment, the pulp suspension is introduced into the elongated chamber 24 through a conduit 19. The device comprises a plurality of modular units 20, 21, 22 and 23, which may be made of metal, glass or plastic, for example. These units fit together, each with a cylindrical central pulp fiber sample chamber 20a, 21a, 22a, 23a collectively to define the elongated cylindrical chamber 24, shown in the Figure in broken lines, and substantially V-shaped. The pulp suspension is transported into chamber 24, and there washed or cleaned. As shown in FIG. 1, the chamber can also be formed in a single housing unit. However a plurality of units can each provide selected amounts of pulp fiber samples. The volume of the chamber 24 also can be increased by using more units 21 and 22, thereby also enabling the volume of pulp samples to be increased.

During its passage through the chamber 24, the pulp suspension passes through an open valve 25. The valve is only schematically illustrated in the Figure, but a ball valve is preferred. Arranged at the bottom of the device is a valve 26 and a conduit 27, for removal of the cleaned pulp. Surplus pulp suspension is discharged through a conduit 28, via a valve 29.

The washing liquid is supplied through conduits 30, 31 and 32. The contaminated washing liquid is transported away through branch conduits 33 and 34, which open into a waste conduit 35. Valves (not shown in the Figure) are incorporated in the conduits 31, 32, 33 and 34 on a level with control devices 36 and 37. The ends 39 and 40 of the chamber 24 are covered with wire cloths (not shown) enclosed in a body 38. The bodies 20, 21, 22 and 23 are of square or rectangular cross-sectional shape, while the cavity 24 is of circular cross-sectional shape.

The manner in which the device according to the invention illustrated in FIG. 2 operates is similar to that of FIG. 1. For example, when the washing liquid is initially introduced through the opening 39 and the contaminated washing liquid removed through opening 40, the valves in the conduits 31 and 33 are open, while the valves in conduits 32 and 34 are closed. Thus, the valves in the conduits 31 and 34 and the valves in the conduits 32 and 33 are out of phase with one another, so that when the control device 36 or the control device 37 closes one valve, the other valve coupled therewith is opened.

In addition to varying the volume of the chamber 24, and thus the amount of pulp sampled, this embodiment has the advantage of eliminating unnecessary chamber capacity. This is significant to the purity of the treated pulp. When connecting valves to a circular elongated chamber, it has been found difficult to avoid the formation of pockets devoid of fibers, which become filled to a greater or lesser extent with contaminated washing liquid. This liquid, which remains in the pockets at the end of the washing accompanies the pulp sample when it is flushed from the apparatus according to the invention.

By shaping units as blocks of square or oblong cross-section, it has been found possible to connect the valves 25, 26 and 29 directly to the periphery of the chamber 24.

In order to illustrate the efficiency of the device according to the invention, a number of tests have been carried out in the form of a working Example, using the device illustrated in FIG. 1.

Pine sulphate pulp in the form of a suspension carrying a quantity pulp equal to one gram bone dry weight, taken downstream of the screening stage after the digester and containing diluted waste cooking liquor, was charged to the tube 1, after which washing liquid in the form of chemically purified water (with a consumption of 0.1 ml 0.1N $KMnO_4$ per 400 ml) was charged alternately to the ends 1a, 1b. The washing stages were run at time intervals of 2, 3 and 4 seconds between the stages, i.e., between changes in the supply of washing liquid, to ascertain the best time interval in the present context.

After washing the pulp only once for a total time of 2, 3, 4 and 6 minutes, the pulp was flushed from the tube with 400 ml of water. The suspension liquid was then separated from the pulp by filtration, and the liquid was analysed with regard to its consumption of potassium permanganate (0.1N $KMnO_4$). The results are given in the Table below.

TABLE 1

| Time intervals between changes in the supply of washing liquid | Potassium permanganate consumption in ml at a total washing time in minutes of: | | | | |
|---|---|---|---|---|---|
| | 2 | 3 | 4 | 5 | 6 |
| 2 | | 9.20 | 2.00 | | |
| 3 | 2.00 | 0.90 | | | 0.15 |
| | 3.90 | 0.95 | 0.60 | | |
| | 3.80 | 0.85 | 0.40 | | |
| | 3.35 | 1.25 | 0.75 | | |
| | 2.60 | 1.60 | 1.00 | | |
| | 2.30 | 0.90 | 0.50 | | |
| 4 | 8.35 | 2.10 | 0.55 | | |
| | 7.85 | 2.50 | 1.05 | | |

Figure 3:
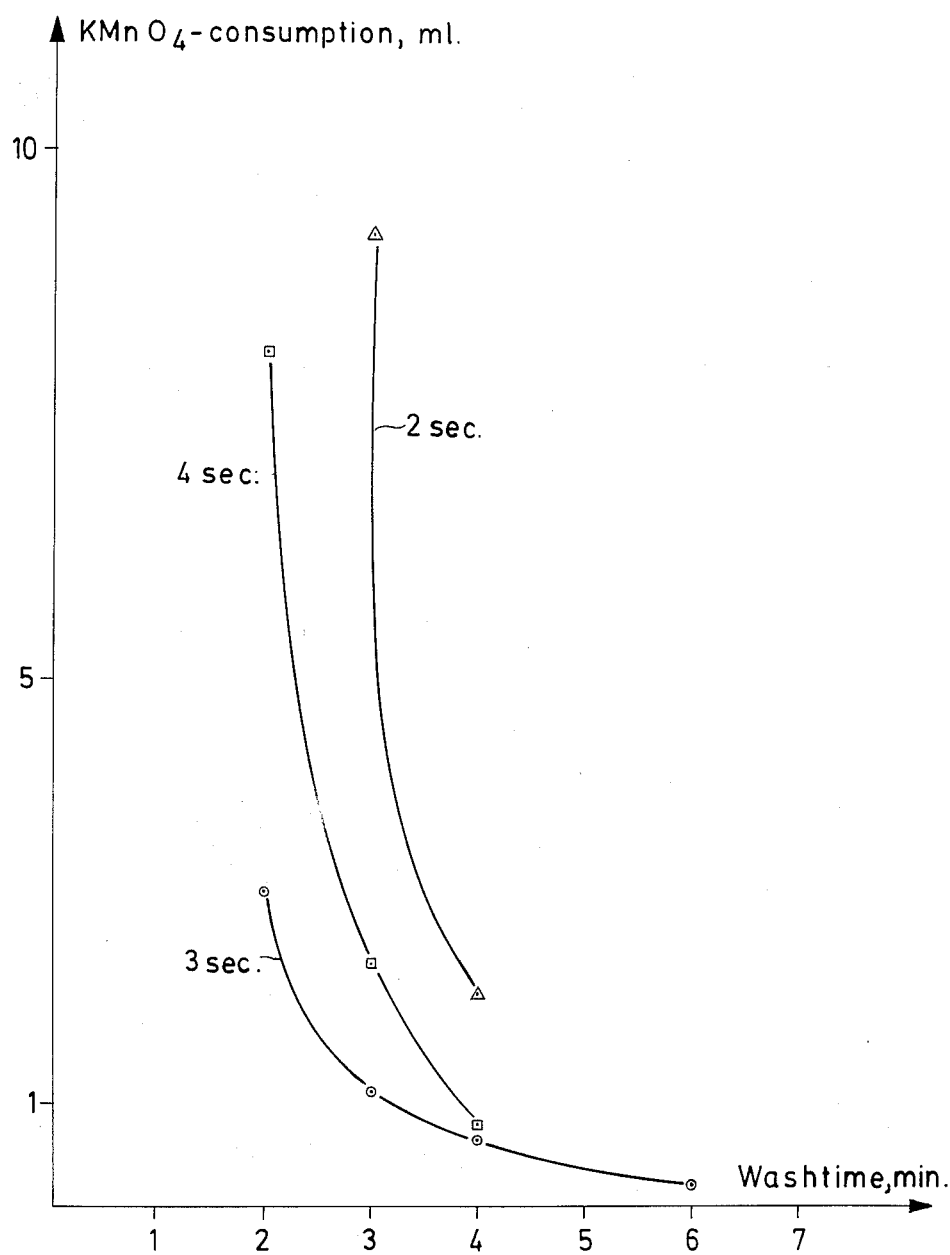
FIG. 3 illustrates the results of tests described in Example 1 and carried out in the device of FIG. 1.

These results are graphed in FIG. 3 in the form of average values.

As shown by the results, a low impurity content of the suspension liquid accompanying the pulp out of the apparatus according to the invention is achieved in a washing time of only 4 minutes. This means that the pulp also has a high degree of purity, since these two parameters are inversely proportional to one another. With this type of pulp (pine) and this kind of impurity (waste cooking liquor), it has been found that the best results are obtained with an interval of three (3) seconds between the changes in the supply of washing liquid, i.e. the impurity content of the suspension liquid is reduced to a low value more rapidly with this time interval. When the pulp is washed over a total washing time of six minutes, while switching the supply of washing liquid at three second intervals, there is obtained a pulp suspension liquid of such purity that it consumes only 0.15 ml permanganate, from which is to be subtracted 0.1 ml permanganate consumed by washing water itself. This means that the actual pulp sample is almost absolutely pure.

Having regard to the foregoing disclosure, the following is claimed as the inventive and patentable embodiments thereof:

1. A closed cellulose pulp fiber sampling and cleaning device for direct fluid flow connection to a flow of cellulose pulp for withdrawing and preparing clean pulp fiber samples for automatic analysis of cellulose pulp fiber properties, comprising:
   (a) a pulp sample receptacle having
      (i) a housing;
      (ii) an elongated pulp fiber sample chamber in the housing, having a central portion, and end portions communicating with and on opposite sides of the central portion, the central portion being lower than either end portion, and having an opening at each end portion;
      (iii) liquid-permeable and pulp fiber-impermeable material covering each opening at each end portion;
      (iv) ports in the housing communicating with the chamber in the lower central portion intermediate the two end portions and with each end portion of the chamber on the outside of the liquid-permeable pulp fiber-impermeable material; and
      (v) valves controlling flow through the ports;
   (b) means for introducing and withdrawing washing liquor through the ports at each end of the chamber;
   (c) means for introducing and withdrawing pulp fiber suspension and withdrawing cleaned pulp fibers through the ports intermediate the two ends; and
   (d) means for closing and opening the valves in synchronization with each other for the alternate supply of washing liquor and removal of contaminated washing liquor, respectively.

2. A device according to claim 1 in which the housing is in the form of a tube that is substantially U-shaped in configuration, the base of the U constituting the lower central portion of the sample chamber.

3. A device according to claim 1 in which the housing is in the form of a tube that is substantially V-shaped in configuration, the base of the V constituting the lower central portion of the sample chamber.

4. A device according to claim 2 or 3 in which a pulp supply conduit is connected to one end of the tube, and a conduit for carrying away surplus pulp suspension is connected to the other end of the tube.

5. A device according to claim 4 in which a conduit for removing cleaned pulp fibers is connected to the tube at the lower central portion intermediate the two ends.

6. A device according to claim 1 in which the liquid-permeable and pulp-impermeable material comprises wire cloth having mesh openings of less than 0.4 mm.

* * * * *